(12) United States Patent
Ghosh

(10) Patent No.: US 10,759,829 B2
(45) Date of Patent: *Sep. 1, 2020

(54) CHROMATOGRAPHY DEVICE AND METHOD FOR FILTERING A SOLUTE FROM A FLUID

(71) Applicant: McMaster University, Hamilton (CA)

(72) Inventor: Raja Ghosh, Dundas (CA)

(73) Assignee: MCMASTER UNIVERSITY, Hamilton (CA)

( * ) Notice: Subject to any disclaimer, the term of this patent is extended or adjusted under 35 U.S.C. 154(b) by 248 days.

This patent is subject to a terminal disclaimer.

(21) Appl. No.: 15/616,333

(22) Filed: Jun. 7, 2017

(65) Prior Publication Data

US 2017/0349626 A1    Dec. 7, 2017

Related U.S. Application Data

(60) Provisional application No. 62/346,709, filed on Jun. 7, 2016.

(51) Int. Cl.
*B01D 15/18*    (2006.01)
*B01D 15/22*    (2006.01)
(Continued)

(52) U.S. Cl.
CPC ............ *C07K 1/18* (2013.01); *B01D 15/18* (2013.01); *B01D 15/22* (2013.01); *B01D 15/30* (2013.01);
(Continued)

(58) Field of Classification Search
CPC ........ B01D 15/18; B01D 15/22; B01D 15/30; B01D 15/362; B01D 15/426; B01D 15/14;
(Continued)

(56) References Cited

U.S. PATENT DOCUMENTS 3,503,712 A * 3/1970 Sussman ................ G01N 30/38
116/18
5,059,654 A * 10/1991 Hou .................. A61K 39/39525
210/198.2

(Continued)

OTHER PUBLICATIONS

Rathore et al., Biopharm Int. 16 (2003) 30-40.
(Continued)

*Primary Examiner* — Katherine Zalasky McDonald
(74) *Attorney, Agent, or Firm* — Bereskin & Parr LLP/S.E.N.C.R.L., S.R.L.

(57) ABSTRACT

A chromatography device for removing a solute from a fluid is provided. The device has a first plate having an inlet and a first channel. The first channel directs the fluid from the inlet towards chromatographic media housed in a chamber coupled to the first plate. The chamber has a leading edge for receiving the fluid from the first channel and a trailing edge for delivering the fluid to a second channel. The chromatographic media is configured to remove the solute from the fluid as the fluid passes through the chamber. The device also has a second plate coupled to the chamber having the second channel and an outlet. The second channel directs the fluid from the chamber to the outlet. The direction of flow of fluid through the first channel and the second channel is transverse to a direction of flow of the fluid through the chromatographic media. A method of removing a solute from a fluid is also provided.

16 Claims, 13 Drawing Sheets

(51) Int. Cl.
*B01D 15/42* (2006.01)
*C07K 1/18* (2006.01)
*C07K 1/16* (2006.01)
*C07K 1/36* (2006.01)
*C07K 14/76* (2006.01)
*C07K 14/765* (2006.01)
*C07K 14/805* (2006.01)
*C12N 9/36* (2006.01)
*B01D 15/36* (2006.01)
*B01D 15/30* (2006.01)
*G01N 30/52* (2006.01)

(52) U.S. Cl.
CPC ......... *B01D 15/362* (2013.01); *B01D 15/426* (2013.01); *C07K 1/16* (2013.01); *C07K 1/36* (2013.01); *C07K 14/76* (2013.01); *C07K 14/765* (2013.01); *C07K 14/805* (2013.01); *C12N 9/2462* (2013.01); *C12Y 302/01017* (2013.01); *G01N 2030/527* (2013.01)

(58) Field of Classification Search
CPC .............. B01D 63/082; B01D 2325/42; G01N 30/6086; G01N 30/6065; G01N 30/6052; G01N 30/60; G01N 30/6017; G01N 30/6091; G01N 30/38; G01N 30/386; G01N 2030/527
See application file for complete search history.

(56) References Cited

U.S. PATENT DOCUMENTS

| | | | |
|---|---|---|---|
| 5,141,635 A | 8/1992 | LePlang et al. | |
| 6,030,539 A * | 2/2000 | Zuk, Jr. ............... | A61M 1/3627 210/188 |
| 6,528,322 B1 * | 3/2003 | Carlsson ................ | G01N 30/94 204/400 |
| 6,565,752 B1 * | 5/2003 | Baron .................... | F04B 43/043 210/175 |
| 8,506,802 B1 * | 8/2013 | de los Reyes ......... | B01D 15/22 210/198.2 |
| 10,195,550 B2 * | 2/2019 | Steen .................... | B01D 29/52 |
| 2003/0052054 A1 * | 3/2003 | Pearl .................... | B01D 63/00 210/500.21 |
| 2004/0000519 A1 * | 1/2004 | Jiang .................. | G01N 30/0005 210/634 |
| 2004/0011648 A1 * | 1/2004 | Paul .................... | B01D 61/18 204/450 |
| 2005/0202557 A1 * | 9/2005 | Borenstein .......... | A61M 1/1678 435/369 |
| 2009/0266756 A1 * | 10/2009 | Fischer-Fruehholz ........................ | B01D 63/10 210/321.83 |
| 2012/0074051 A1 * | 3/2012 | Gebauer ............ | G01N 30/6017 210/198.2 |
| 2012/0223015 A1 * | 9/2012 | Browning ............... | A61M 1/16 210/646 |
| 2014/0197101 A1 * | 7/2014 | Harjes .................... | A61M 1/16 210/637 |
| 2014/0339170 A1 * | 11/2014 | de los Reyes ....... | B01D 15/206 210/656 |
| 2017/0182433 A1 * | 6/2017 | de los Reyes ........ | B01D 15/22 |
| 2017/0252672 A1 * | 9/2017 | Ghosh ................... | B01D 15/22 |
| 2017/0349626 A1 * | 12/2017 | Ghosh ................... | B01D 15/18 |
| 2018/0236378 A1 * | 8/2018 | Ghosh ............... | B01D 15/1885 |

OTHER PUBLICATIONS

Ghosh, J. Chromatogr. A 1468 (2016) 164-172.
Ghosh, J. Chromatogr. A 952 (2002) 13-27.
Charcosset, J. Chem. Technol. Biotechnol. 71 (1998) 95-110.
Svec et al., Anal. Chem. 87 (2014) 250-273.
Mallik et al., J. Sep. Sci. 29 (2006) 1686-1704.
Anspach et al., J. Chromatogr. A 865 (1999) 129-144.
Jungbauer, Trends Biotechnol. 31 (2013) 479-492.
Kelley, Biotechnol. Prog. 23 (2007) 995-1008.
Hanke et al., Trends Biotechnol. 32 (2014) 210-220.
Ferreira et al., Trends Biotechnol. 18 (2000) 380-388.
Gallant et al., J. Chromatogr. A 725 (1996) 295-314.
Levison, J. Chromatogr. B 790 (2003) 17-33.
Low et al., J. Chromatogr. B 848 (2007) 48-63.
Ghosh et al., J. Membr. Sci. 516 (2016) 36-32.
Stickel et al., Biotechnol. Prog. 17 (2001) 744-751.
Yuan et al., J. Chromatogr. A 831 (1999) 149-165.
Lode et al., J. Chromatogr. A 796 (1998) 3-14.
Hereijgers et al., J. Chem. Technol. Biotechnol. 90 (2015) 2122-2131.
Smits et al., J. Chromatogr. A 1369 (2014) 125-130.
Johnson et al., Biotechnol. Prog. 30 (2014) 837-844.
Camenzuli et al., Analyst 136 (2011) 5127-5130.
Broyles et al., J. Chromatogr. A 917 (2001) 1-22.
Shalliker et al., J. Chromatogr. A 1335 (2014) 122-135.
Madadkar et al., J. Membr. Sci. 487 (2015) 173-179.
Madadkar et al., J. Membr. Sci. 499 (2016) 126-133.

* cited by examiner

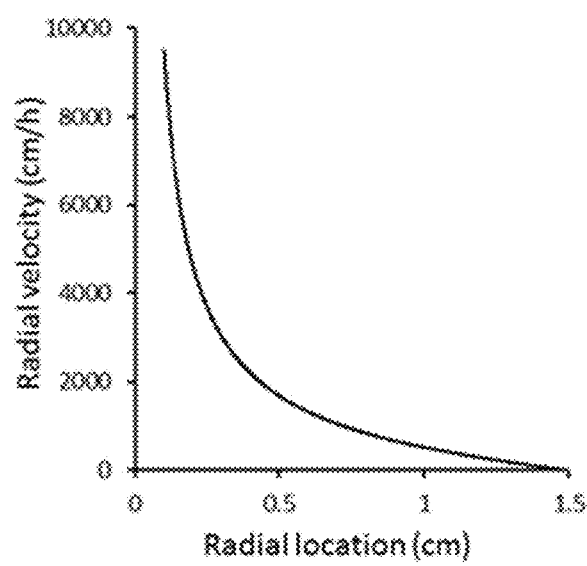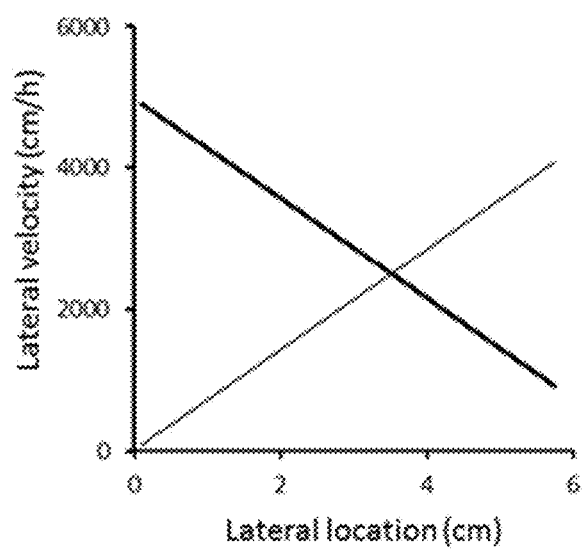
FIG. 8A                                      FIG. 8B

CHROMATOGRAPHY DEVICE AND METHOD FOR FILTERING A SOLUTE FROM A FLUID

CROSS-REFERENCE TO RELATED APPLICATION

This application claims priority to U.S. Provisional Application No. 62/346,709 filed on Jun. 7, 2016, the entire contents of which are hereby incorporated herein by reference.

TECHNICAL FIELD

The following relates to a chromatography device and more specifically to a packed-bed chromatography device

BACKGROUND

Large-scale or process chromatography is almost entirely carried out using columns. While membranes, monoliths and other alternatives are gradually finding acceptance in niche applications such as biopharmaceutical purification, the use of columns in chromatography continues.

Process chromatography is widely used for the purification of biopharmaceuticals such as monoclonal antibodies, interferons, growth factors and vaccines. One of the major attributes of columns used in such applications is their small bed-height to diameter ratio. Chromatographic separation processes are commonly scaled-up by increasing the column diameter while maintaining the bed height constant. Several factors make is necessary to use such columns. Firstly, the pressure drop increases with bed-height and beyond a certain point becomes a limiting factor. Also, columns with small bed-heights and larger cross-sectional areas can be operated at significantly higher flow rates than tall columns of similar bed-volumes, and are therefore more productive.

Columns are easy to pack with a stationary phase and the flow of mobile phase is axis-symmetric. Samples can therefore be conveniently distributed in a symmetric fashion over its entire cross-section, and it is easy to visualize the segregation of separated bands of solutes as they move gradually towards the outlet. Also, a circular cross-section gives the maximum bed-volume per unit conduit perimeter and this is a vital factor when designing large packed-bed devices in general.

Chromatographic resins used for bioseparation tend to be "soft" and more compressible compared to those used in other applications. Consequently, in a tall column, the sheer weight of resin could result in severe compaction in material closer to the bottom, leading to inconsistencies in separation.

The use of columns with small bed-height to diameter (i.e. axial to radial dimension) ratios gives rise to some major engineering challenges. Achieving uniform flow distribution within such columns is difficult. During sample injection, non-uniform distribution may result in distortion of the sample front within the column. Similarly, during elution, the eluent front could get distorted. Overall, these factors result in radial and axial dispersion effects which results in broad and poorly resolved eluted peaks, which ultimately affect purity, recovery and productivity of a separation process. Peak broadening also results in the dilution of the material eluted from a column which in turn could represent loss of process efficiency, due to the need for downstream concentration steps.

SUMMARY

In one aspect, a process chromatography device for removing a solute from a fluid is provided, the device has a first plate having an inlet and a first channel, the first channel for directing a fluid from the inlet towards a chromatographic media. The device also has a chamber which houses the chromatographic media, coupled to the first plate. The chamber has a leading edge for receiving the fluid from the first channel and a trailing edge for delivering the fluid to a second channel, the chromatographic media being configured to remove the solute from the fluid as the fluid passes through the chromatographic media; and a second plate coupled to the chamber, the second plate having the second channel and an outlet, the second channel for directing the fluid from the chamber to the outlet; wherein the first channel directs the fluid over the leading edge of the chamber in a direction that is transverse to a direction of flow of the fluid through the chromatographic media and the second channel directs fluid from the trailing edge of the chamber to the outlet in a direction that is transverse to the direction of flow of the fluid through the chromatographic media.

In some other embodiments, the inlet is positioned on a first side of the first plate to receive fluid into the device and direct the fluid towards the first channel in a direction transverse to the direction of flow of the fluid through the first channel.

In some other embodiments, the outlet is positioned on a first side of the second plate to receive the fluid from the second channel and direct the fluid out of the device in a direction transverse to the direction of flow of the fluid through the second channel.

In some other embodiments, the inlet is laterally aligned with the leading edge of the chamber.

In some other embodiments, the outlet is laterally aligned with the trailing edge of the chamber.

In some other embodiments, the inlet is laterally offset from the leading edge of the chamber.

In some other embodiments, the outlet is laterally offset from the trailing edge of the chamber.

In some other embodiments, a width of the first channel increases along its length from the inlet to the leading edge of the chamber to distribute the fluid across the resin as the fluid exits the first channel.

In some other embodiments, the width of the first channel increases along its length at a constant rate from the inlet to the leading edge of the chamber.

In some other embodiments, the width of the first channel increases along its length at a variable rate from the inlet to the first surface of the resin.

In some other embodiments, a width of the second channel decreases along its length from trailing edge of the chamber to the outlet to collect the fluid from the chamber.

In some other embodiments, the width of the second channel decreases along its length at a constant rate from the trailing edge of the chamber to the outlet.

In some other embodiments, the width of the second channel decreases along its length at a variable rate from the trailing edge of the chamber to the outlet.

In some other embodiments, the first channel comprises a structure to distribute the fluid across the first channel and over the leading edge of the chamber.

In some other embodiments, the structure is a mesh.

In some other embodiments, the structure is a plurality of pillars.

In another aspect, a chromatography device for removing a solute from a fluid is provided. The device has a first plate having a fluid flow in a first direction to direct the fluid across a first surface of a resin; a chamber housing the resin, the fluid directed through the resin in a second direction to remove the solute from the fluid; and a second plate having a fluid flow in a third direction for collecting the fluid from the chamber; wherein the first direction and the third direction are transverse to the second direction.

In another aspect, a method of removing a solute from a fluid is provided. The method includes directing the fluid through a first plate in a first direction and over a first surface of a resin; directing the fluid through the resin in a second direction to remove the solute from the fluid, the resin housed in a cavity of a chamber; and directing the fluid through a second plate in a third direction, the second plate for collecting the fluid from the resin. The first direction and the third direction are transverse to the second direction.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

The drawings included herewith are for illustrating various examples of articles, methods, and apparatuses of the present specification. In the drawings:

FIG. 8A is a graph showing simulated values for radial velocity as function of radial location in the plate of the 9 mL Capto Q media containing column ($v_s$=42.4 cm/h, column radius=1.5 cm, h=0.05 cm);

FIG. 8B is a graph showing simulated values for lateral velocity as function of location in the upper and lower lateral channels of the 9 mL Capto Q media containing chromatobox ($v_s$=42.4 cm/h, channel length=5.89 cm, channel width=1.2 cm, h=0.05 cm, thick line: upper channel, thin line: lower channel);

DETAILED DESCRIPTION

Various apparatuses or processes will be described below to provide an example of each claimed embodiment. No embodiment described below limits any claimed embodiment and any claimed embodiment may cover processes or materials that differ from those described below. The claimed embodiments are not limited to materials or processes having all of the features of any one material or process described below or to features common to multiple or all of the materials described below. It is possible that a material or process described below is not covered by any of the claimed embodiments. Any embodiment disclosed below that is not claimed in this document may be the subject matter of another protective instrument, for example, a continuing patent application, and the applicants, inventors or owners do not intend to abandon, disclaim or dedicate to the public any such embodiment by its disclosure in this document.

It will be understood that the terms "top" and "bottom" referred to herein are used in the context of the attached Figures. The terms are not necessarily reflective of the orientation of the process chromatography device in actual use and are therefore not meant to be limiting in their use herein.

Described herein are various embodiments for a process chromatography device for removing solute from a fluid. The device has three main components: a first plate, a chamber and a second plate.

To filter solutes from the fluid, generally, fluid enters the device at an inlet of the first plate positioned at a first end of the device and is distributed laterally over a first side (e.g. feed side) of a chromatographic media (e.g. a resin) therein. The fluid enters the resin at different locations along a length and width of the first side of the resin and flows through the resin in a direction transverse to the first surface of the resin. The fluid emerges from the resin through a second surface (e.g. permeate side) of the resin and is collected by a second channel. The fluid flows laterally with respect to the second surface of the resin through the second channel towards a device outlet positioned at a second end of the device. The lateral-flows through the first channel and the second channel (e.g. the direction of travel of the fluid prior to and over the first side (e.g. on the feed side) of the resin and after emerging through the second side (e.g. on the permeate side) of the resin) are transverse to the direction of flow of the fluid through the resin. Further, the first channel can be used to distribute the influent fluid on the feed-side of the resin while the second channel can be used to collect the effluent fluid on the permeate side of the resin. This flow arrangement may simplify balancing a pressure-drop across the chamber and may provide consist flux (or superficial velocity). This design may also provide consistent solute flow path lengths throughout the packed bed and thereby reduce residence time distribution.

Figure 1:
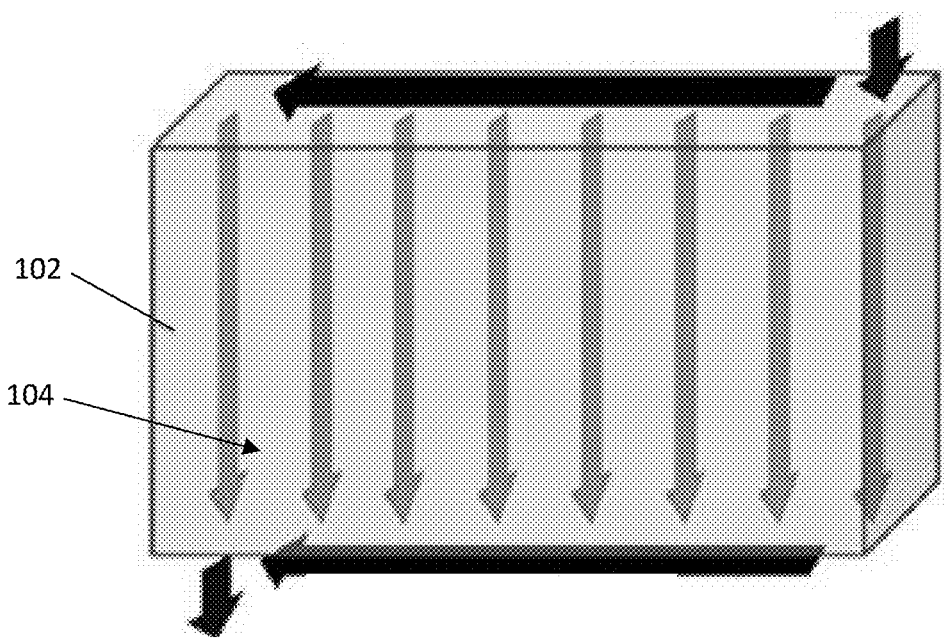
FIG. 1 is a schematic diagram of one embodiment of a chromatography device with idealized flow paths.

Turning to the Figures, FIG. 1 shows exemplary flow pathways of fluid through a chamber 102 housing a resin 104. In the embodiment shown, fluid can be provided to the chamber 102 in a direction that is parallel to the direction of flow of the fluid through the chamber (i.e. through the resin). In other embodiments, fluid can be provided to chamber 102 in a direction that is transverse to the direction of flow of the fluid through the chamber (i.e. through the resin 104).

As is described below, as fluid enters the chamber 102 through an inlet (not shown), the fluid disperses across a first side of the chamber 102 in a direction transverse to the direction of flow of the fluid through the resin 104. As the fluid passes over the resin 104, a portion of the fluid falls through the resin 104 (e.g. by gravity). After passing through the resin 104, the fluid is collected across a second side of the chamber 102 towards an outlet (not shown). Movement of the fluid through chamber 102 is described in more detail below.

Figure 2:
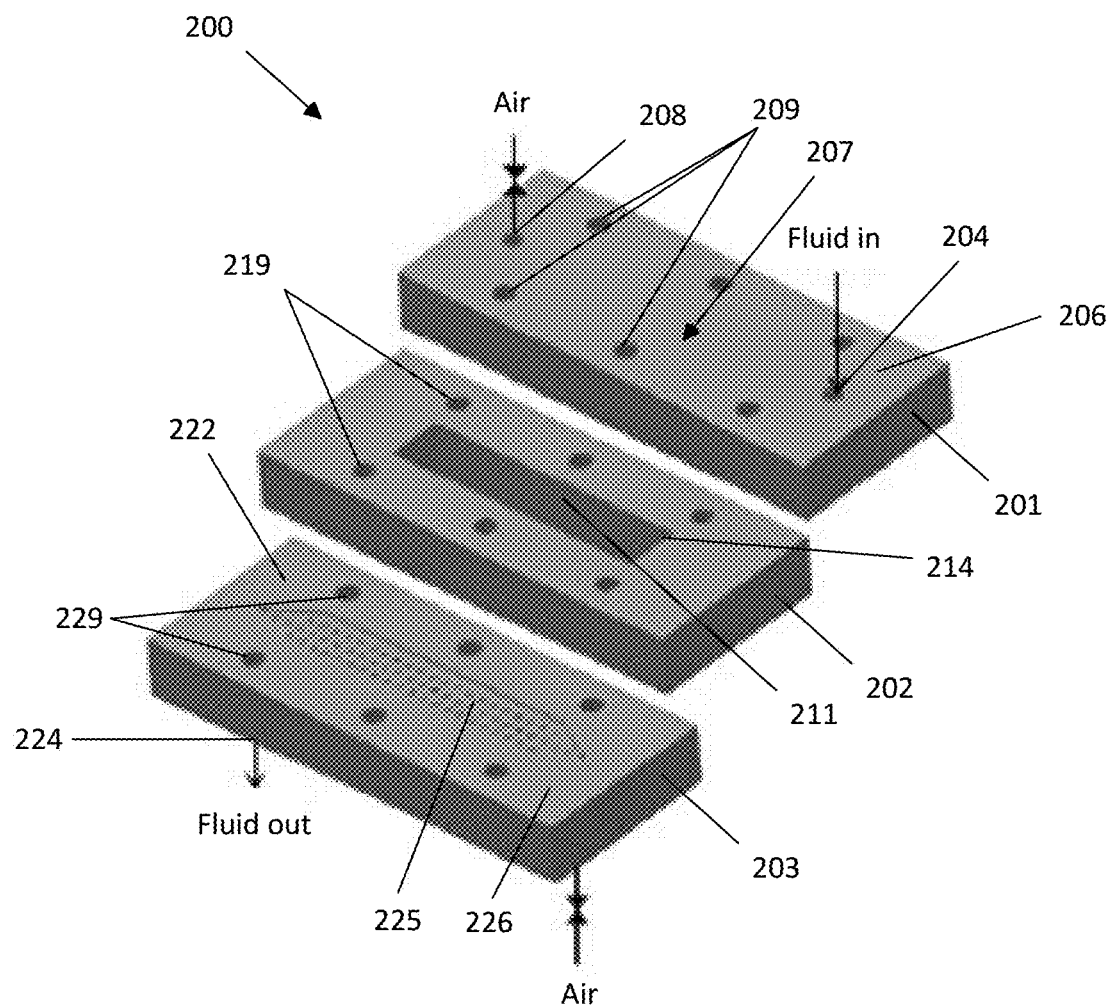
FIG. 2 is a schematic diagram showing an exploded perspective view of another embodiment of a chromatography device.

FIG. 2 shows an exploded perspective view of an embodiment of a chromatography device 200. Device 200 comprises a first plate 201, a chamber 202 and a second plate 203.

First plate 201 comprises an inlet 204, a first channel 205 (not shown), and a first body 206. Fluid enters the device 200 through inlet 204 formed in body 206 of first plate 201. Inlet 204 can be any appropriate inlet (e.g. a port or aperture extending through body 206). In the embodiment shown in FIG. 2, inlet 204 is an aperture that extends from a first surface 207 of device 200 through body 206 of first plate 201 and is in fluid communication with first channel 205. Inlet 204 directs fluid entering the chromatography device 200 towards chamber 202 via first channel 205. In other embodiments, inlet 204 can extend from another outer surface of device 200 through first plate 201 to direct fluid from outside of the device 200 towards chamber 202.

First channel 205 is fluidly connected to inlet 204 and carries fluid from inlet 204 towards chamber 202. As such, inlet 204 is upstream of first channel 205 and first channel 205 is upstream of chamber 202.

The term upstream can be defined as direction of fluid flow experienced by (i.e. away from) a position on a flow pathway (i.e. channel or through the chamber) relative to the direction experienced by (i.e. towards) another position on the same flow pathway (i.e. channel or through the chamber). For example, a location A of a flow pathway (e.g. first channel 205) is considered upstream of a relative location B of the same flow pathway if, at location A, fluid is flowing away from location A and towards location B.

Accordingly, the term downstream can be defined as direction of fluid flow experienced by (i.e. towards) a position on a flow pathway (i.e. channel or through the chamber) relative to the direction experienced by (i.e. away from) another position on the same flow pathway (i.e. channel or through the chamber). For example, a location A of a flow pathway (e.g. first channel 205) is considered downstream of a relative location B of the same flow pathway if, at location A, fluid is flowing towards location A from location B.

Returning to the embodiment shown in FIG. 2, first channel 205 can be defined by first body 206 of first plate 201 (e.g. embedded in first plate 201 and/or formed by first plate 201). For example, first channel 205 can be recessed into plate 201. In the embodiment shown in FIG. 2, inlet 204 is positioned along first body 206 such that fluid entering device 200 via inlet 204 is carried by first channel 205 towards chamber 202 in a direction that is parallel to a direction of flow of the fluid through chamber 202. Put another way, in the embodiment shown in FIG. 2, as a fluid is received by inlet 204, the fluid has a direction of flow that is parallel (e.g. the same or similar) to a direction of flow of the fluid through the resin 210 of chamber 202. Additionally, in the embodiment shown in FIG. 2, inlet 204 is positioned to be spaced from a leading edge 214 of chamber 202 such that fluid travelling along first channel 205 passes over leading edge 214 before passing through resin 210.

First plate 201 can optionally have a vent 208 to vent device 200 (e.g. provide for movement of air into and out of device 200). First plate 201 can also optionally have a plurality of apertures 209 for securing first plate 201 to chamber 202 and/or second plate 203. First plate 201 can be secured to chamber 202 and/or second plate 203 in any appropriate manner (e.g. screws, bolts, pins, adhesives, etc.).

In the embodiment shown in FIG. 2, chamber 202 is positioned between first plate 201 and second plate 203. Accordingly, chamber 202 is downstream of first plate 201 and upstream of second plate 203. Chamber 202 is positioned inferior to (e.g. below) first plate 201 and superior to (e.g. above) second plate 203.

Chamber 202 defines cavity 211 for housing (e.g. accommodating) resin 210 (not shown). Cavity 211 has an inner wall 212 for housing resin 210 therein. Inner wall 212 extends through chamber 202 such that, when plate 201 is placed on top of chamber 202, cavity 211 is substantially aligned with first channel 205 so fluid can flow through first channel 205 along a first surface (e.g. top surface) of resin 210 filling cavity 211.

To inhibit movement of resin 210 in cavity 211, chamber 202 can include a mesh (not shown). The mesh can be positioned such that the mesh retains resin 210 in chamber 202. Each opening in the mesh should be small enough to effectively retain individual resin particles of resin 210 in cavity 211 while providing for the fluid to pass therethrough (e.g. to pass from the first channel 205 to the second channel 225 through cavity 211. In one specific example, the mesh can be a nylon mesh having a 0.002 inch opening (product number 9318T48, McMaster Carr, USA) to retain resin particles larger than 90 microns in diameter. The mesh may be coupled to chamber 202 to provide support thereto. In some embodiments, the mesh may be coupled to first plate 201 or second plate 203.

Chamber 202 also has a leading edge 214 and a trailing edge 217 (not shown). Leading edge 214 of cavity 211 is a boundary that the fluid crosses while approaching cavity 211 from first channel 205. Once fluid has passed leading edge 214 it can descend through resin 210 of chamber 202. Leading edge 214 receives fluid from first channel 205 (e.g. is fluidly coupled to first channel 205) of device 200. Trailing edge 217 is a boundary that fluid crosses while exiting cavity 211 and approaching outlet 224. Fluid that has passed through resin 210 is collected by second channel 225 and guided to outlet 224 such that the fluid passes trailing edge 217 while travelling towards outlet 224 (e.g. trailing edge 217 is fluidly coupled to second channel 225). Trailing edge 217 is both laterally opposed to leading edge 214 and vertically opposed to leading edge 214. For example, trailing edge 217 is laterally spaced from leading edge 214 by a length of cavity 211 and vertically spaced from leading edge 214 by a height of cavity 211 (e.g. by a height of inner wall 212).

As fluid travels along first channel 205 and approaches resin 210, fluid is distributed laterally over first surface (not shown) of resin 210. As the fluid exits first channel 205 and enters resin 210, the direction of flow of the fluid changes. For example, as the fluid enters (e.g. falls through) the resin 210 the fluid travels in a direction that is transverse (e.g. orthogonal) to the direction that the fluid travelled along first channel 205, eventually emerging at corresponding locations of a second surface where the fluid flows laterally to the outlet 224 of the device 200. The fluid enters resin 210 at different locations along a length and a width of the first surface (not shown) of resin 210 (e.g. at different locations along a length and width of cavity 211).

Figure 3:
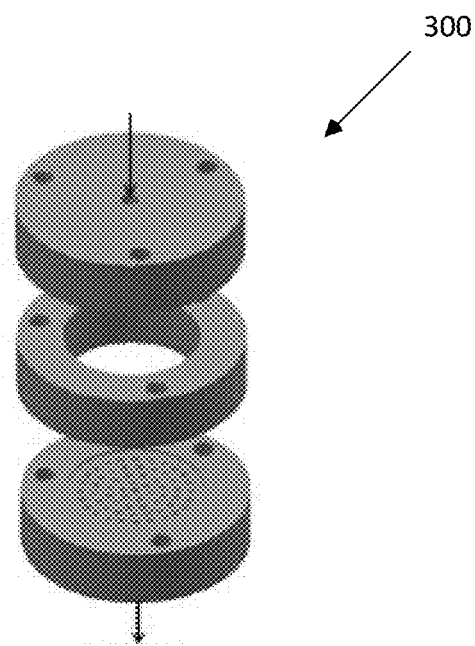
FIG. 3 is a schematic diagram showing an exploded perspective view of a chromatography column.

This configuration makes it possible to balance the pressure-drop on the feed side with that on the permeate side, thereby ensuring uniformity of flow along the length of the resin 210. Also, unlike a radial-flow device (such as that shown in FIG. 3), where the superficial velocity within the bed increases in a radially inward direction (see for example FIG. 4), the flow of fluid through device 200 can be more uniform (e.g. fluid passing through a greater proportion of the resin 210 when compared to radial-flow prior art devices). As shown in FIG. 1, the fluid has a flow path length that is independent of where the fluid enters the chamber 202 (e.g. resin 210). Therefore, the device 200 can provide for fluid passing there through to have a consistent path length through the device. This may improve the efficiency of resin utilization and the resolution of eluted peaks in chromatographic separation.

Chamber 202 is designed to house a resin 210. Resin 210 can be any suitable adsorbent or size-exclusion type chromatographic media which could be either particulate or fibrous or in the form of sheets. For example, in one embodiment, resin 210 may be a cation exchange chromatography medium. In another embodiment, resin 210 may be appropriate for protein separation or separation of other biomolecules. Resin 210 can be incorporated into device 200 in any appropriate manner. In one specific example, Capto S strong cation exchange media can be used as the resin 210.

Chromatography device 200 can be made of any appropriate material. In one example, the chromatography device 200 can be made of a Delrin acetal resin (e.g. Delrin® (Dupont)).

After the fluid has passed through resin 210 (e.g. to remove a solute therefrom), the fluid emerges from resin 210 at different locations along a length and a width of a second surface (not shown) of resin 210 (e.g. at different locations along a length and width of cavity 211) and enters second channel 225. As the fluid exits resin 210 and enters second channel 225, the direction of flow of the fluid changes. For example, as the fluid enters the second channel 225, the fluid travels in a direction that is transverse (e.g. orthogonal) to the direction that the fluid travelled through resin 210. Second channel 225 collects the fluid and carries the fluid away from the second surface (not shown) of resin 210 towards outlet 224.

Second channel 225 can be defined by second body 226 of second plate 203 (e.g. embedded in second plate 203 and/or formed by second plate 203). For example, second channel 225 can be recessed into second plate 203. In the embodiment shown in FIG. 2, outlet 224 is positioned along second body 226 such that fluid exiting chamber 202 is carried by second channel 225 towards outlet 226 in a direction that is transverse to a direction of flow of the fluid through chamber 202. Put another way, in the embodiment shown in FIG. 2, as a fluid is received by outlet 224, the fluid in travelling in a direction that is transverse (e.g. the same or similar) to a direction of flow of the fluid through the resin 210 of chamber 202. FTo pass through outlet 224, the direction of flow of the fluid changes to be parallel to the direction of flow of the fluid through chamber 202. Additionally, in the embodiment shown in FIG. 2, outlet 224 is positioned to be spaced from trailing edge 217 of chamber 202 such that fluid travelling along second channel 225 passes trailing edge 217 after passing through resin 210 and before passing through outlet 224.

In one embodiment, first channel 205 and second channel 225 can have an irregular shape. For example, as first channel 205 extends laterally from inlet 204 to leading edge 214, a width of first channel 205 can increase over the length of first channel 205. In one embodiment, the width of the first channel 205 can increase at a constant rate over its length (e.g. taper). In another embodiment, the width of the first channel 205 can increase at a variable rate over its length (e.g. rounded). An irregular (e.g. tapered or rounded) shape of first channel 205 may provide for distribution of the fluid over the leading edge 214 of chamber 202 as fluid is provided by first channel 205 from inlet 204 to chamber 202.

Similarly, in another embodiment, as second channel 225 extends laterally from trailing edge 217 to outlet 224, a width of second channel 225 can decrease over the length of second channel 225. For example, a width of the second channel 225 can decrease at a constant rate over its length (e.g. taper) or at a variable rate over its length (e.g. rounded). An irregular (e.g. tapered or rounded) shape of second channel 225 may provide for collection of the fluid from trailing edge 217 of chamber 202 as fluid is provided by second channel 225 from chamber 202 to outlet 224.

In some examples, first channel 205 and second channel 225 can each, independently, have a structure therein to disrupt the flow of fluid there through. For example, first channel 205 and second channel 225 can comprise a mesh layer (e.g. a structure having a pattern to disrupt flow within the channels 205,225). In some examples, the mesh layer (not shown) within first channel 205 and second channel 225 can have a same thickness as first channel 205 and second channel 225, respectively. In another example, a plurality of pillars (e.g. microcolumns) can be provided within first channel 205 and second channel 225 to disrupt the flow of fluid there through.

Structures (e.g. spacers) as described herein positioned in channels 205,225 can be used to provide each of channels 205,225 with similar lateral resistance over the sides (e.g. first surface (e.g. top surface) and second surface (e.g. bottom surface) of resin 210 and/or leading edge 214 and trailing edge 217) of the chamber 202. The structures can also provide support for resin 210 and may reduce dead volume within device 200. In one specific example, before assembling the device 200, channels 205,225 may be provided with 70 mm×20 mm pieces of woven wire mesh (approximately 0.5 mm thick).

Chamber 202 can also have a plurality of apertures 219 extending there through for securing chamber 202 to first plate 201 and/or second plate 203. As described above, first plate 201 can be secured to chamber 202 and/or b second plate 203 in any appropriate manner (e.g. screws, bolts, pins, adhesives, etc.).

The fluid passing though resin 201 of chamber 202 emerges from a second surface (not shown) of resin 210 into second channel 225. Second channel 225 can be formed into a body 226 of second plate 203 (as shown in FIG. 2). Second channel 225 is configured to direct fluid received from chamber 202 in a direction transverse to a direction of flow of the fluid through resin 210 to outlet 224 of device 200. The direction of flow of the fluid through second channel 225 is transverse to the direction of flow of fluid through chamber 202 and can be the same direction as the direction of fluid through first channel 205.

Second plate 203 as shown in FIG. 2 can also define a plurality of apertures 229 extending there through for securing second plate 203 to chamber 202 and/or first plate 201. As described above, first plate 201 can be secured to chamber 202 and/or second plate 203 in any appropriate manner (e.g. screws, bolts, pins, adhesives, etc.).

First plate 201, chamber 202 and second plate 203 are generally made of polymer-based materials. In one example, first plate 201, chamber 202 and second plate 203 can be acrylic and 3D printed using a commercially available 3D printer (e.g. ProJet HD3000 printer by 3D Systems (Rock Hill, S.C., USA)). In another example, first plate 201, chamber 202 and second plate 203 can be formed by polymer molding.

EXAMPLES

The following Examples were carried out using a chromatography device (hereinafter also referred to as a "chromatobox") containing 9 mL of Capto S strong cation exchange media and an equivalent (or control) column (i.e. having identical bed-height and volume, and thereby same cross-sectional area). The shapes of flow-through and eluted protein peaks are compared. Separation of different model binary protein mixtures was carried out and the resolutions of the peaks thus obtained are compared.

Strong cation exchange Capto S (product number 17-5441-01) chromatographic media was purchased from GE Healthcare Biosciences, QC, Canada. Proteins lysozyme (pI=11.0, catalog number L6876), bovine serum albumin (pI=4.8, catalog number A7906), human hemoglobin (pI=6.9, catalog number H7379) and conalbumin (pI=6.0-6.6, catalog number C0755), and chemicals used to prepare buffer were purchased from Sigma-Aldrich (St. Louis, Mo., USA). All buffers and the solutions were prepared using water obtained from a SIMPLICITY 185 water purification unit Millipore (Molsheim, France). Buffers and solutions used in chromatography experiments were micro-filtered and degassed prior to use.

The chromatography devices used in these Examples and its equivalent (or control) column were designed and fabricated in-house. These were made of white Delrin acetal resin (product number 8573K123, McMaster-Carr, USA). The design of the device was according to one of the embodiments described above. The equivalent column (see FIG. 3) consisted of a circular frame provided with a circular slot to house the packed-bed, with plates on both sides. These plates were provided with pillars similar to those in the lateral channels of the chromatography device, to facilitate flow distribution and collection.

The rectangular packed-bed dimensions within the chromatography box device were 58.9 mm (length)×12 mm (width)×12.7 mm (height), corresponding to an effective bed-volume of 9 mL. The column had a 30 mm packed-bed diameter and a bed-height of 12.7 mm. The bed-height to diameter ratio of the column was 0.42, which was fairly typical for process-scale chromatography columns used in the biopharmaceutical industry.

In both devices, the respective packed-beds were separated from the plates (or lateral channels) using a nylon mesh (0.002 inch opening, product number 9318T48, McMaster Carr, USA). The mesh retained the resin within the device, and also served as an anti-jetting feature. During the chromatography experiments, the box or column used was integrated with an AKTA prime liquid chromatography system (GE Healthcare Biosciences, QC, Canada) using peak tubing, and samples were injected using appropriate sample loops.

Figure 4:
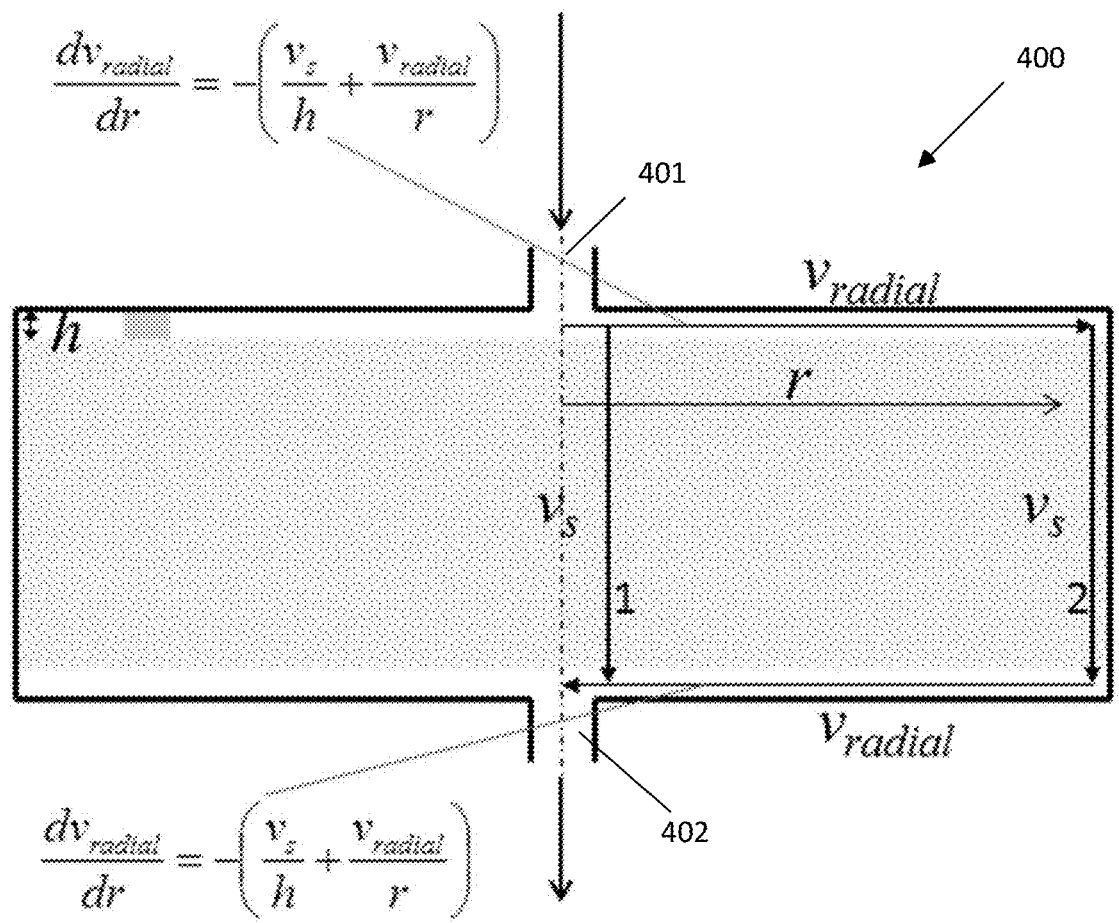
FIG. 4 is a cross-sectional view of the chromatography device of FIG. 3 showing a section drawing having a small bed-height to diameter ratio.

FIG. 4 shows a section of a column 400 with a low bed-height to diameter ratio. The liquid is distributed from inlet 401 in the first plate (not shown) in a radially outward direction and is collected at outlet 402 in the lower plate (not shown) in a radially inward direction. As can be seen in the figure, this flow arrangement results in significant variability in the hydraulic path lengths (l), e.g. a path closer to the centre (1) will be shorter than one closer to the periphery (2):

$$l_2 > l_1 \qquad (1)$$

While the superficial velocity ($v_s$) within the packed bed remained fairly uniform, the radial velocity ($v_r$) in the first plate would decrease in an outward direction (r) due to increase in available cross-sectional area, as well as due to loss of liquid by flow into the packed-bed. By performing mass balance over a control volume between radial locations r and r+δr in the first plate it can be shown that:

$$\frac{dv_r}{dr} = -\left(\frac{v_r}{r} + \frac{v_s}{h}\right) \qquad (2)$$

Where h is the height of column plate/lateral channel.

The above equation which is undefined at r=0 but valid for all other values of r implies that the radial velocity in the first plate would decrease very significantly closer to the centre, and to a lesser extent closer to the periphery. In the lower plate, the radial velocity would increase in a radially inward direction due to decrease in available cross-sectional area, and cumulative collection of liquid from the packed bed. For the same radial location, the radial velocity in the lower plate would be of the magnitude as in the first plate, but in the opposite direction. If we assume that the superficial (or axial) velocity within the packed-bed is uniform, the average fluid velocity along path 1 would be greater than that along path 2:

$$\upsilon_1 > \upsilon_2 \quad (3)$$

Such variation of radial velocity in a plate has been demonstrated using tracer experiments dyes in earlier studies. Therefore, the hydraulic residence time ($\tau = l/\upsilon$) along path 2 would be considerably greater than that along path 1:

$$\tau_2 \gg \tau_1 \quad (4)$$

Such radial variability in solute residence time within a packed-bed, which has also been reported in the literature could be expected to contribute in a significant way towards peak broadening and consequently loss of peak-resolution.

Figure 5:
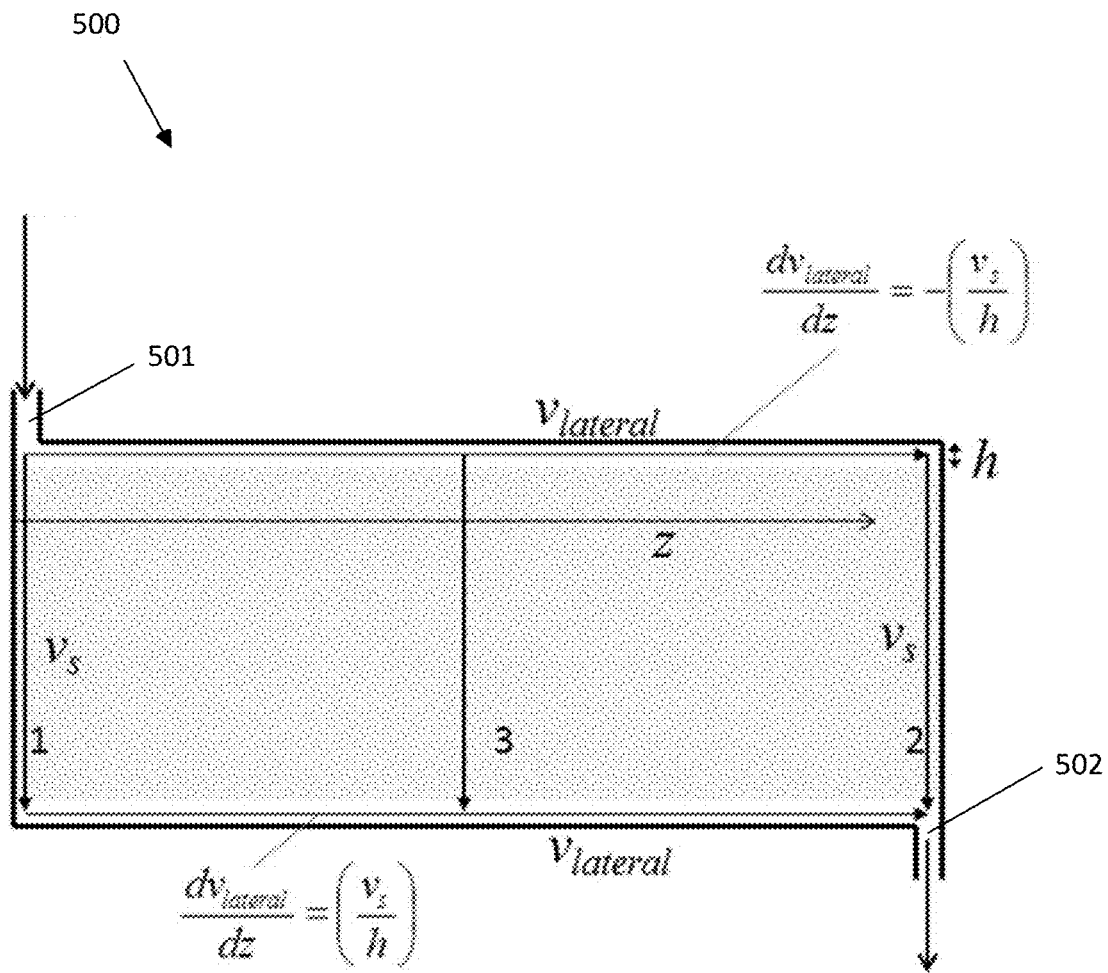
FIG. 5 is a cross-sectional view of the chromatography device of FIG. 2 showing a section drawing of a chromatography box.

FIG. 5 shows, in another embodiment, a cross-section of a chromatobox 500 with low bed-height to length ratio. As can be seen in the figure, this flow arrangement results in uniformity in the hydraulic path lengths, e.g. path 1 (closer to the inlet 501) will be of the same length as path 2 (closer to the outlet 502).

$$l_2 = l_1 \quad (5)$$

Uniform superficial velocity in a packed-bed housed within a chromatography box device could be guaranteed by satisfying two sets of conditions. First, the pressure drop along the length (z) of the two lateral channels should be the same, i.e.:

$$\frac{dP_U}{dz} = \frac{dP_L}{dz} \quad (6)$$

Where $P_L$, is the pressure drop in lower lateral channel, and $P_U$ is the pressure drop in lower lateral channel.

Secondly, the pressure drop across the packed bed should be greater than the pressure drop in these lateral channels. Assuming uniform superficial velocity and performing a mass balance over a control volume between locations z and z+Δz in the first lateral channel, it could be shown that:

$$\frac{d\upsilon_z}{dz} = -\frac{v_s}{h} \quad (7)$$

Where $\upsilon_z$ is the lateral velocity.

The above equation suggests that the lateral velocity would decrease linearly along the length of the first channel. Such linear decrease in fluid velocity in lateral channels of LFMC devices have been demonstrated using tracer dye experiments in earlier studies. Performing a mass balance in the lower channel of the chromatography box, it could be shown that:

$$\frac{d\upsilon_z}{dz} = \frac{v_s}{h} \quad (8)$$

Therefore, the fluid velocity in the lower lateral channel would increase linearly along the length of the device. The average fluid velocity along paths 1 and 2 would therefore be the same:

$$\upsilon_1 = \upsilon_2 \quad (9)$$

So the solute residence time along paths 1 and 2 would be identical.

$$\tau_1 = \tau_2 \quad (10)$$

From equations (7) and (8), it could be shown that the sum of the lateral velocities in the first and second channels for a given lateral location z is equal to the lateral velocity at the inlet of the first channel, i.e. remains constant. Let us consider path 3 located somewhere within the device between paths 1 and 2 (see FIG. 5). For the segment of the path in the first channel, i.e. from the inlet to where the path enters the packed bed, the velocity decreases at the rate ($\upsilon_s/h$), while for the segment of the path in the second channel, i.e. from where it emerged from the packed bed to the outlet, the velocity increases at the rate ($\upsilon_s/h$). The same would be true from any such path within the chromatobox device. Based on this, it could be assumed that the residence time would not vary significantly with the lateral location of the flow path. This has been verified using numerical calculations (see FIG. 9B).

Initial experiments were carried out using BSA as unbound tracer protein to characterize the hydraulics of the 9 mL Capto S media containing column and chromatobox. The mobile phase used in these experiments was 20 mM sodium phosphate (pH 6.0), at a flow rate of 5 mL/min (0.55 bed volumes per minute, vs=42.4 cm/h). Table 1 and 2 summarize the data from the peaks obtained by injecting 100 and 250 µL respectively 1 mg/mL BSA solution (prepared in the mobile phase).

TABLE 1

Comparison of BSA flow-through peaks obtained with column and chromatobox (media: Capto S cation exchange, bed volume: 9 mL, flow rate: 5 mL/min, vs = 42.4 cm/h; BSA concentration: 1 mg/mL, buffer: 20 mM sodium phosphate pH 6.0, loop: 100 µL).

| Device | $w_{0.5}$ (mL) | a (mL) | B (mL) | AF | $v_R$ (mL) |
|---|---|---|---|---|---|
| Chromatobox | 1.10 | 1.01 | 1.02 | 1.01 | 3.95 |
| Column | 1.90 | 1.55 | 2.3 | 1.48 | 3.89 |

TABLE 2

Comparison of BSA flow-through peaks obtained with column and chromatobox (media: Capto S cation exchange, bed volume: 9 mL, flow rate: 5 mL/min, vs = 42.4 cm/h; BSA concentration: 1 mg/mL, buffer: 20 mM sodium phosphate pH 6.0, loop: 250 µL).

| Device | $w_{0.5}$ (mL) | a (mL) | B (mL) | AF | $v_R$ (mL) |
|---|---|---|---|---|---|
| Chromatobox | 1.19 | 1.08 | 1.09 | 1.01 | 4.02 |
| Column | 1.95 | 1.51 | 2.33 | 1.54 | 3.98 |

Figure 6:
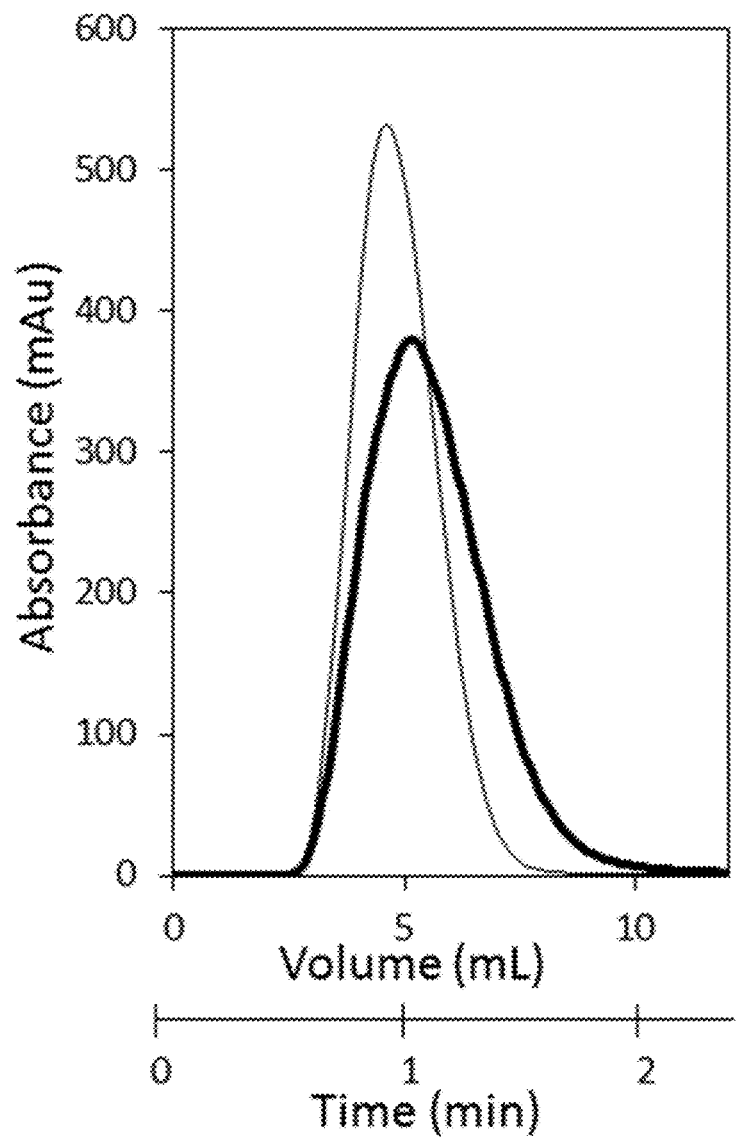
FIG. 6 is a graph showing unbound (or flow-through) protein peak obtained with column and box device (protein: BSA; concentration: 5 mg/mL; loop: 2 mL; buffer: 20 mM sodium phosphate, pH 6.0; flow rate: 5 mL/min; packed-bed volume: 9 mL; media: Capto S; thin line: box; thick line: column)

The peaks obtained with the chromatobox were significantly sharper and more symmetric than those obtained with the column. These experimental results are consistent with expectations based on the above theoretical analysis on residence time distribution, i.e. equations (1-10). From the peak characteristics, it may be inferred that the flow distribution within the chromatobox was more uniform than in the column, and its solute residence time distribution was significantly narrower. FIG. 6 shows the BSA (unbound) flow-through peaks obtained by injecting 2 mL of 5 mg/mL BSA solution. As in the experiments carried out using smaller volume of protein solution, the peak obtained with the chromatobox was sharper than that obtained with the column. The maximum absorbance values were 532 mAu and 379 mAu, the peak width as half height being 2.1 and 3.0 mL, and the asymmetry factors (AF) being 1.14 and 1.56 respectively for the chromatobox and the column. AF was calculated from the ratio of the rear and front segment of a peak at 10% peak height.

The number of theoretical plates in the two sets of columns and chromatoboxes was determined using sodium chloride as freely diffusible trace molecule. The mobile phase used in these experiments was 0.4 M sodium chloride while 0.8 M sodium chloride was used as the tracer. The experiments with the 9 mL devices were carried out at 5 mL/min flow rate (vs=42.4 cm/h) while those with the 50 mL devices were carried out at 6.6 mL/min (vs=31.54 cm/h). The volume of tracer injected in these experiments was ~1% of the respective packed-bed volume. In the experiments carried out using 9 mL of Capto S media, a 0.1 mL loop was used, while in those carried out using 50 mL Capto Q media, a 0.5 mL loop was used. The peak retention volume and peak width at half height were measured from the conductivity profiles thus obtained and the number of theoretical plates (N) was calculated using the equation shown below:

$$N = 5.545 \left(\frac{V_R}{w_{0.5}}\right)^2 \quad (11)$$

Where $V_R$ is the residence volume and $w_{0.5}$ is the peak width at half-height.

The peak variance ($\sigma^2$) was calculated using the following equation:

$$\sigma^2 = (0.42466\overline{w}_{0.5})^2 \quad (12)$$

Where $\overline{w}_{0.5}$ is the normalized peak width at half-height.

Table 3 summarizes the data obtained using the 9 mL Capto S column and chromatobox while Table 4 summarizes the corresponding data obtained from the 50 mL Capto Q experiments.

TABLE 3

Determination of the number of theoretical plates in the 9 mL Capto S media containing column and chromatobox (mobile phase: 0.4M sodium chloride, tracer: 0.8M sodium chloride, flow rate: 5 mL/min, vs = 42.4 cm/h; loop: 0.1 mL)

| Device | $V_R$ (mL) | $w_{0.5}$ (mL) | AF | $\overline{N}$ (/m) | $\sigma^2$ |
|---|---|---|---|---|---|
| Column | 9.3 | 3.9 | 1.013 | 2628 | 0.0317 |
| Chromatobox | 9.2 | 2.9 | 1.004 | 4651 | 0.0179 |

TABLE 4

Determination of the number of theoretical plates in the 50 mL Capto Q media containing column and chromatobox (mobile phase: 0.4M sodium chloride, tracer: 0.8M sodium chloride, flow rate: 6.6 mL/min, vs = 31.54 cm/h; loop: 0.5 mL).

| Device | $V_R$ (mL) | $w_{0.5}$ (mL) | AF | $\overline{N}$ (/m) | $\sigma^2$ |
|---|---|---|---|---|---|
| Column | 43.5 | 7.5 | 1.132 | 4908 | 0.0054 |
| Chromatobox | 41.5 | 6.7 | 1.098 | 5598 | 0.0047 |

The number of theoretical plates per metre ($\overline{N}$) obtained with 9 mL column was low while that obtained with the 50 mL column was consistent with that reported in the literature for process columns filled with Capto Q media. These results demonstrate that column maldistribution due to inadequate fluid scaling has a more significant impact on the performance of columns having low bed height to diameter ratios. The number of theoretical plates per metre obtained with the two chromatobox devices was comparable to that reported in the literature for commercial Capto S and Capto Q based columns having ~20 cm bed heights. However, quantifying efficiency of preparative columns, particularly those with low bed-height to diameter ratios in terms of either plate height or number is not without its pitfalls. When tracer of ~1% bed volume is injected in these columns, the likelihood of solute reaching the wall of the column before reaching the outlet is quite low. It has been widely reported that efficiency of analytical separations can be enhanced using "infinite diameter" columns. However, the scope and objectives of preparative separations is to use the packed-bed binding capacity to the maximum extent possible. Consequently, these separations are carried out using much larger sample volumes than in analytical chromatography, typically comparable to the column volume. Therefore, the utility of the plate height or number determination for assessing relative efficiency of preparative columns, particularly those with small bed-height to diameter ratios is somewhat questionable.

Figure 7:
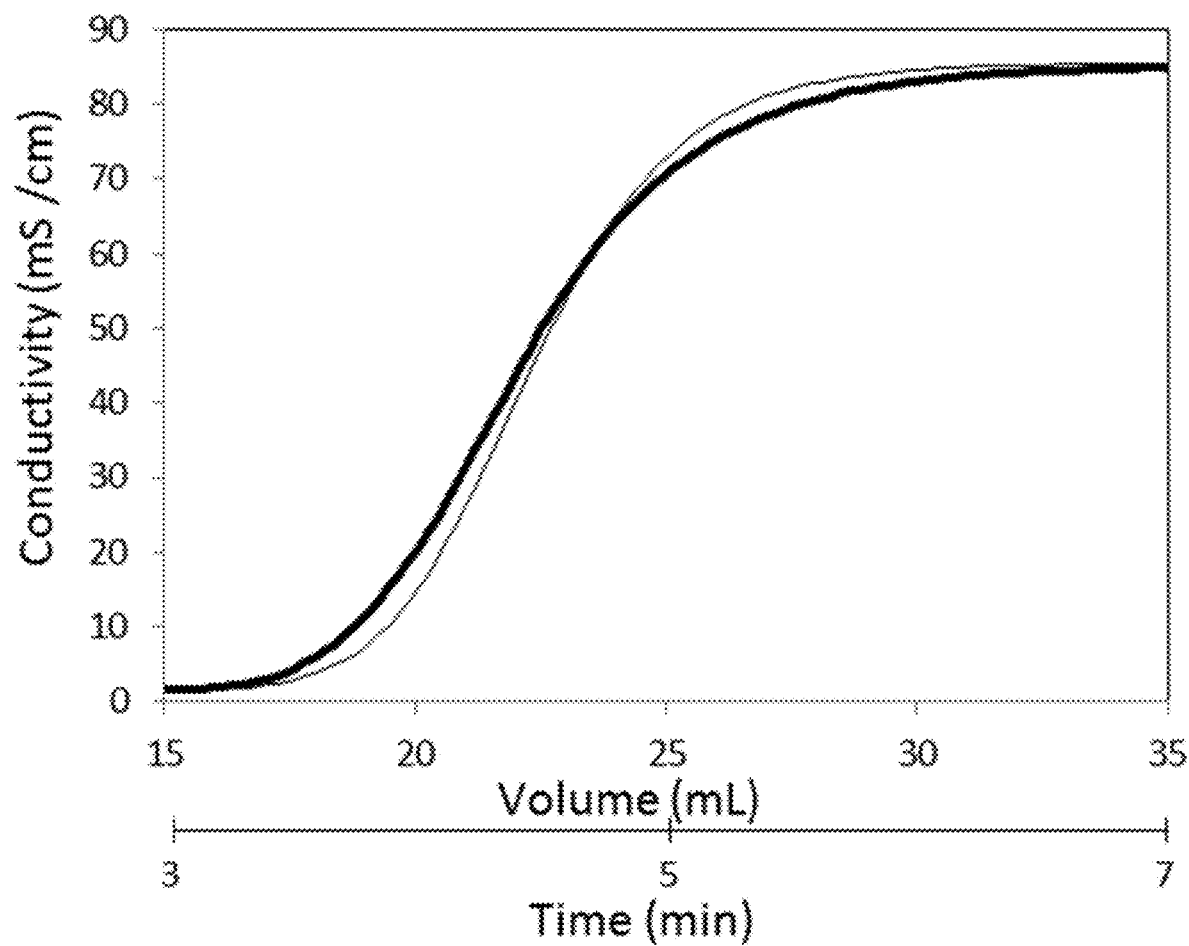
FIG. 7 is a graph showing salt breakthrough curves obtained with the column device shown in FIG. 3 and the box device shown in FIG. 2 (buffer A: 20 mM sodium phosphate, pH 6; buffer B: 1 M NaCl prepared in buffer A; step change to 100% buffer B after 10 mL; flow rate 5 mL/min) $v_s$=42.4 cm/h; packed-bed volume: 9 mL; media: Capto S; thin line: chromatobox; thick line: column)

FIG. 7 shows the salt breakthrough curves obtained with the 9 mL chromatobox and column by step-change from sodium chloride-free buffer (20 mM sodium phosphate, pH 6.0) to 1 M sodium chloride-containing buffer. Both these experiments were carried out at 5 mL/min flow rate ($v_s$=42.4 cm/h). Sodium chloride-free buffer was initially passed through these devices to obtain stable conductivity baselines. The results shown in the figure were obtained by making the step-changes to 100% sodium chloride containing buffer approximately 10 mL after stable baseline was obtained, and the instant the step-change was made is designated time zero. The salt breakthrough obtained with the chromatobox was sharper than that obtained with the column, with the breakthrough taking place slightly later and the saturation taking place slightly earlier. These results, which are consistent with the expectations form the theoretical plate analysis and the unbound protein pulse experiments discussed in the previous paragraphs, indicated once again that the solute residence time distribution within the chromatobox was narrower and dispersion effects within it were lower. In order to verify this, equation (2) was used to simulate the radial velocity in the column plates and equations (7) and (8) were used to simulate the lateral velocities in the upper and lower lateral channels of the chromatobox. As stated earlier, equation (2) is undefined at r=0. Therefore, the initial data point for radial velocity was calculated based on mass balance at r=0.1 cm and found to be 9511.7 cm/h. This information was used to calculate the subsequent radial velocity values from 0.101 to 1.499 cm radial location, at 0.001 cm interval. FIG. 8A shows the simulated values for radial velocity in the first column plate as function of radial location. For the same radial location, the radial velocity in the lower plate would be of magnitude but in the opposite direction, i.e. radially inward. The huge variability in radial velocity could be expected to lead to variability in residence time within the column. For the chromatobox, the initial velocity data point was obtained by mass balance at 0.1 cm lateral location and found to be 4915.2 cm/h. This information was used to calculate the subsequent lateral velocity values from 0.101 to 5.890 cm lateral location, at 0.001 cm interval. FIG. 8B shows the simulated values for lateral velocity in the upper and lower channels of the chromatobox as function of lateral location.

Figure 9A:
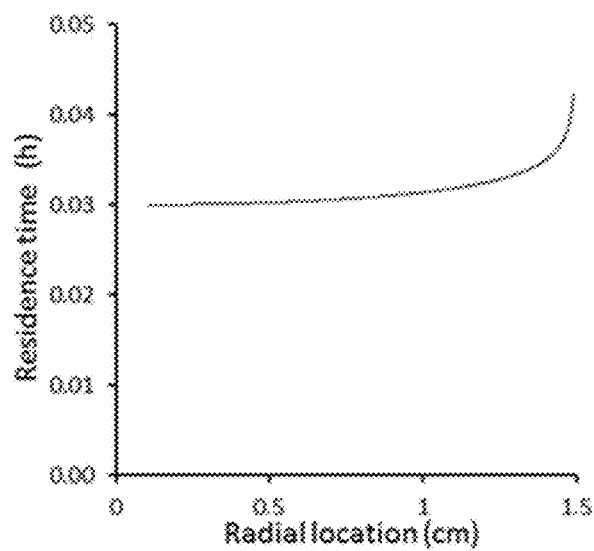
FIG. 9A is a graph showing simulated values for residence time as function of radial location in the 9 mL Capto Q media containing column ($v_s$=42.4 cm/h, bed height=1.27 cm, column radius=1.5 cm, h=0.05 cm)
Figure 9B:
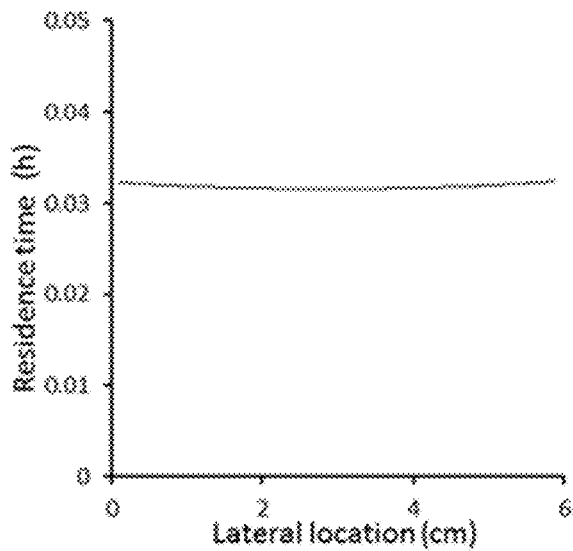
FIG. 9B is a graph showing simulated values for residence time as function of lateral location in the 9 mL Capto Q media containing chromatobox ($v_s$=42.4 cm/h, bed height=1.27 cm, channel length=5.89 cm, channel width=1.2 cm, h=0.05 cm)

The radial and lateral velocity data shown in FIGS. 8 A and B was used to calculate the residence times corresponding to the different radial locations of the column, and lateral locations of the chromatobox device. The results thus obtained are shown in FIGS. 9 A and B respectively. For both devices, i.e. column and chromatobox, the superficial velocity within the respective packed bed was assumed to be uniform, i.e. location independent. As hypothesized earlier and as shown in FIG. 9A, the residence time within the column varied with radial location, increasing sharply towards the periphery. The residence time within the chromatobox device did not vary significantly with lateral location (see FIG. 9B), the value being slightly lower in the central regions of the device. Based on the above, it may be anticipated that the 9 mL chromatobox would give better chromatographic separation than the 9 mL column.

Figure 10:
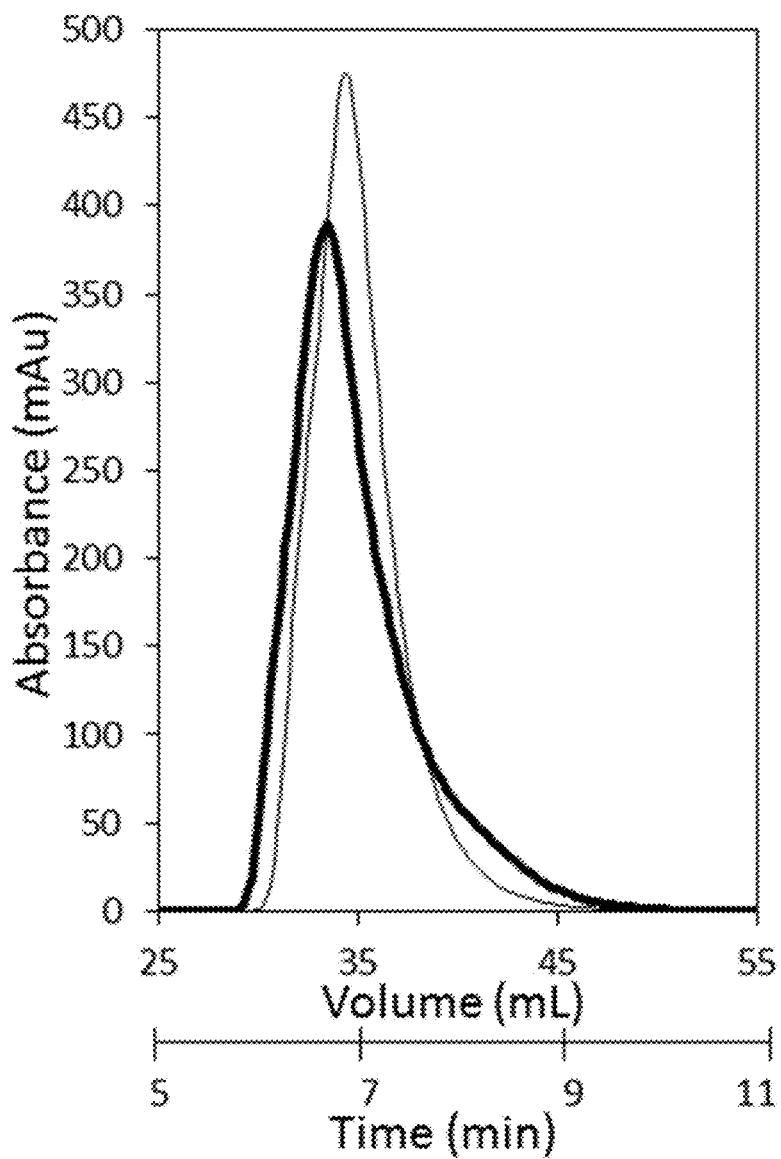
FIG. 10 is a graph showing bound and eluted lysozyme peak obtained with column and chromatobox (protein: lysozyme; concentration: 5 mg/mL; loop: 1 mL; binding buffer: 20 mM sodium phosphate, pH 6.0; eluting buffer: 1 M sodium chloride, prepared in buffer A; flow rate: 5 mL/min; $v_s$=42.4 cm/h; elution: step change after 20 mL; packed-bed volume: 9 mL; media: Capto S; thin line: chromatobox; thick line: column)

FIG. 10 shows the bound and eluted protein (lysozyme) peaks obtained using the 9 mL Capto S column and chromatobox by injecting 1 mL of 5 mg/mL lysozyme solution prepared in 20 mM sodium phosphate buffer, pH 6.0 (binding buffer). The mobile phase flow rate used in these experiments was 5 mL/min (0.55 bed volumes per minute, $v_s$=42.4 cm/h) and the peaks were obtained by step change to 1 M sodium chloride, 20 mL after sample injection. The eluted peak obtained with the chromatobox was sharper and narrower than that obtained with column. The peak widths at half-height were 4 mL and 5 mL respectively, while the asymmetry factors were 1.43 and 2.59 respectively, for the chromatobox and the column. The above results provide further evidence that laterally-fed design feature of the chromatobox could potentially address the problem of maldistribution in packed-bed devices, particularly those with short bed heights.

Figure 11A:
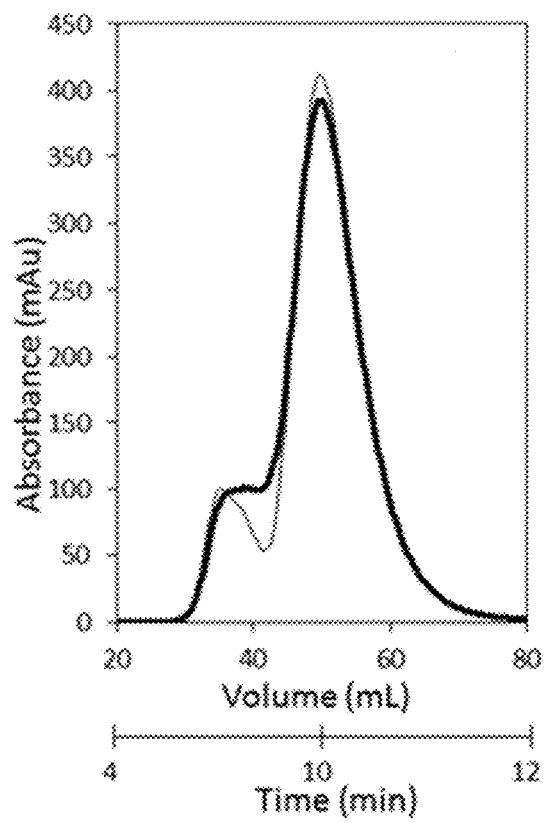
FIG. 11A is a graph showing. separation of conalbumin and lysozyme with column and chromatobox (protein mixture: 2.5 mg/mL lysozyme+0.5 mg/mL conalbumin; loop: 5 mL; binding buffer: 20 mM sodium citrate, pH 4.9; eluting buffer: 0.5 M sodium chloride, prepared in buffer A; flow rate: 5 mL/min; $v_s$=42.4 cm/h; elution: 20 mL gradient after 10 mL; packed-bed volume: 9 mL; media: Capto S; thin line: chromatobox; thick line: column)
Figure 11B:
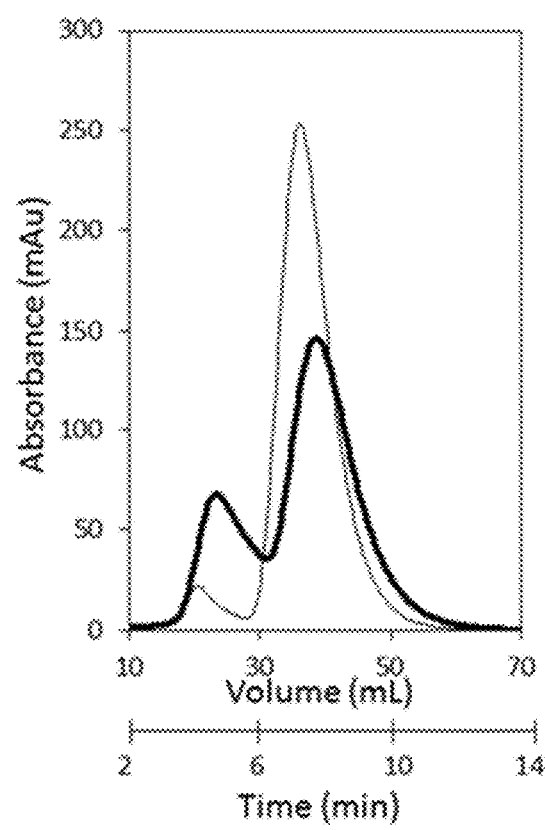
FIG. 11B is a graph showing separation of conalbumin and lysozyme with column and chromatobox (protein mixture: 2.5 mg/mL lysozyme+0.5 mg/mL conalbumin; loop: 2 mL; binding buffer: 20 mM sodium citrate, pH 5.5; eluting buffer: 0.5 M sodium chloride, prepared in buffer A; flow rate: 5 mL/min; $v_s$=42.4 cm/h; elution: 15 mL gradient after 5 mL; packed-bed volume: 9 mL; media: Capto S; thin line: chromatobox; thick line: column)

FIG. 11A shows the chromatograms for binary protein (conalbumin and lysozyme) separation carried out using the 9 mL Capto S media containing column and the chromatobox. In these experiments, which were carried out at 5 mL/min flow rate (0.55 bed volumes per minute, vs=42.4 cm/h), 20 mM sodium citrate buffer (pH 4.9) used as binding buffer, while 0.5 M sodium chloride was used as eluent. A 5 mL loop was used for sample (0.5 mg/mL conalbumin+2.5 mg/mL lysozyme) injection, and a 20 mL linear gradient to 100% eluting buffer was initiated 10 mL after sample injection. At this experimental condition, conalbumin and lysozyme were partially resolved by the chromatobox. The resolution obtained with the column was poorer, with the conalbumin appearing as a shoulder adjacent to the lysozyme peak. FIG. 11B shows the chromatograms for conalbumin and lysozyme separation carried out using the 9 mL column and the chromatobox at a slightly different experimental condition than that used in the experiments described above. Here, 20 mM sodium citrate buffer (pH 5.5) was used as binding buffer, with 2 mL of sample (0.5 mg/mL conalbumin+2.5 mg/mL lysozyme) being injected. The flow rate was 5 mL/min (0.55 bed volumes per minute, $v_s$=42.4 cm/h) while a 15 mL linear gradient to 100% eluting buffer (i.e. 0.5 M sodium chloride) was applied 5 mL after sample injection. While almost baseline resolution of the eluted peaks was obtained with the chromatobox, the peaks obtained with the column were only partially resolved. Interestingly, the conalbumin peak obtained with the column was pushed up by the adjacent lysozyme peak, giving the chromatogram an appearance inconsistent with the composition of the binary protein mixture (i.e. 1:5 conalbumin to lysozyme concentration ratio). These results show that the chromatobox device is suitable for carrying out high-resolution protein separation.

Figure 12:
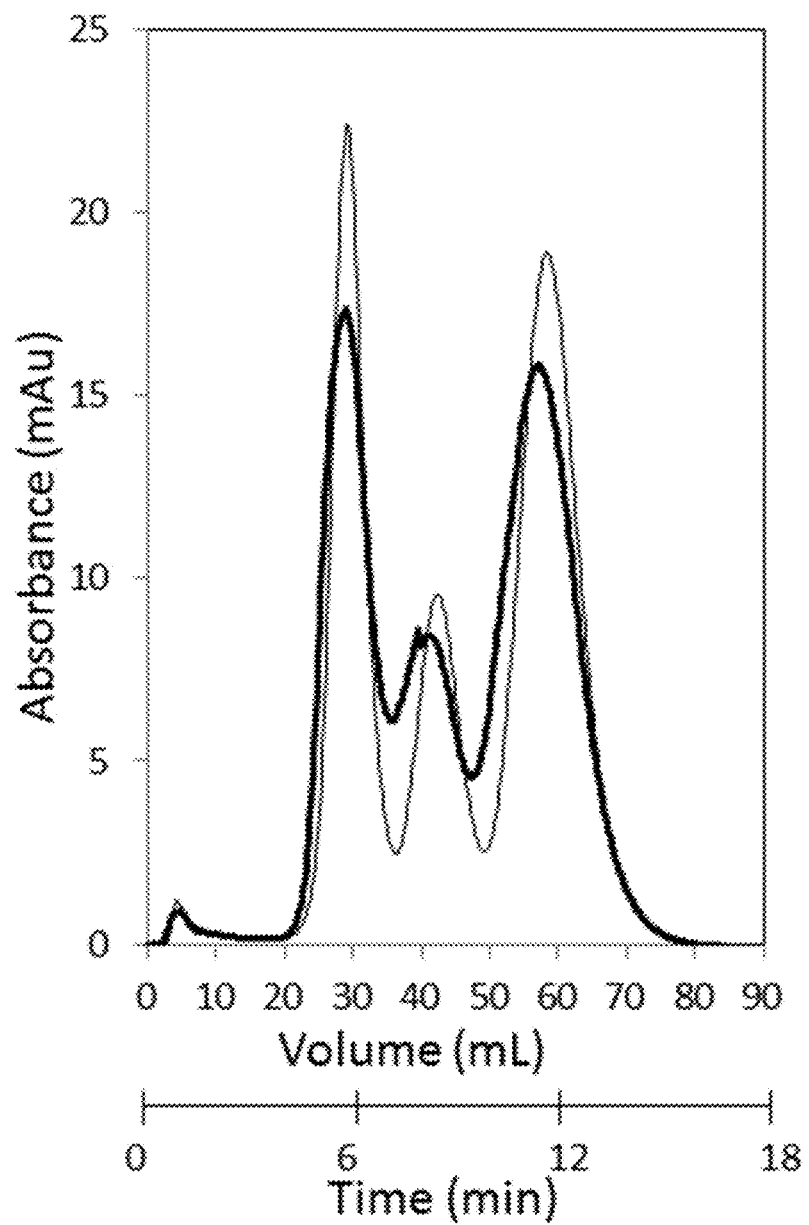
FIG. 12 is a graph showing separation of myoglobin, ribonuclease A and lysozyme with column and chromatobox (protein mixture: 0.5 mg/mL myoglobin+0.66 mg/mL ribonuclease A+0.5 mg/mL lysozyme; loop: 1 mL; binding buffer: 20 mM sodium phosphate, pH 6; eluting buffer: 0.5 M sodium chloride, prepared in buffer A; flow rate: 5 mL/min; $v_s$=42.4 cm/h; elution: 40 mL gradient after 10 mL; packed-bed volume: 9 mL; media: Capto S; thin line: chromatobox; thick line: column)

FIG. 12 shows the chromatograms obtained during the separation of a ternary protein mixture consisting of myoglobin, ribonuclease A and lysozyme, carried out using the 9 mL Capto S media containing column and the chromatobox. These experiments were carried out at 5 mL/min flow rate (0.55 bed volumes per minute, vs=42.4 cm/h) using 20 mM sodium phosphate buffer (pH 6) as binding buffer, and 0.5 M sodium chloride as eluent. A 1 mL loop was used for sample (0.5 mg/mL myoglobin+0.66 mg/mL ribonuclease A+0.5 mg/mL lysozyme) injection, and a 40 mL linear gradient to 100% eluting buffer was initiated 10 mL after sample injection. Consistent with the results obtained with binary protein mixture (shown in FIG. 10), the resolution obtained with the chromatobox was better than that obtained with the column.

Figure 13:
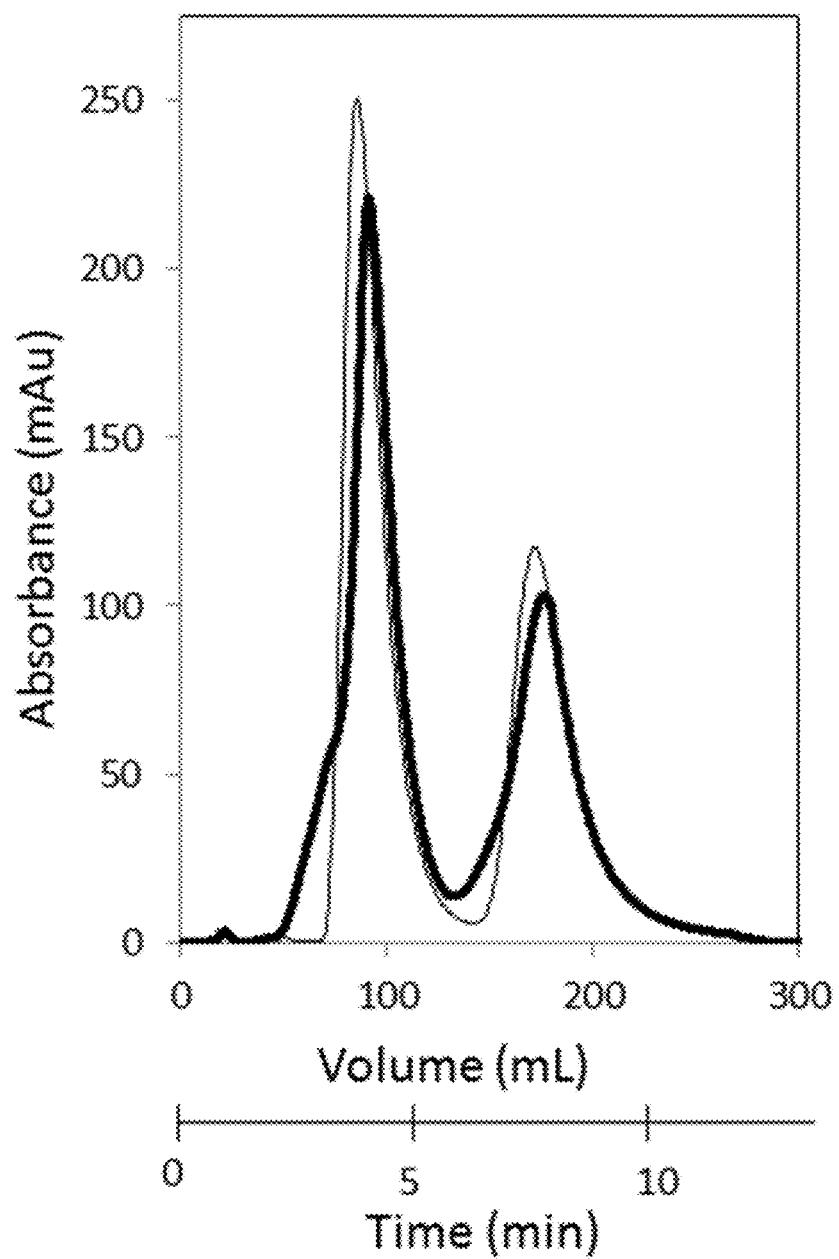
FIG. 13 is a graph showing separation of myoglobin and BSA with column and chromatobox (protein mixture: 10 mg/mL myoglobin+20 mg/mL BSA; loop: 2 mL; binding buffer: 20 mM Tris, pH 8.5; eluting buffer: 0.5 M sodium chloride, prepared in buffer A; flow rate: 21.9 mL/min; $v_s$=100 cm/h; elution: A 200 mL gradient after 10 mL, B 250 mL after 10 mL; packed-bed volume: 50 mL; media: Capto Q; thin line: chromatobox; thick line: column).

FIG. 13 shows the chromatograms obtained during the separation of myoglobin and BSA using the 50 mL Capto Q media containing chromatography column and chromatobox. These experiments were carried out 21.9 mL/min flow rate (0.438 bed volumes per minute, $v_s$=100 cm/h) using 20 mM Tris buffer (pH 8.5) as binding buffer and 0.5 M sodium chloride at eluent. The feed solution contained 10 mg/mL myoglobin and 20 mg/mL BSA, and 2 mL of this solution was injected in these experiments. A 200 mL linear gradient to 100% eluting buffer was initiated 10 mL after sample injection. The peak obtained around 100 mL effluent volume was due to the myoglobin while the second peak in both chromatograms (i.e. retention volume ~190 mL) was due to BSA. As observed in the earlier experiments carried out using the 9 mL Capto S media containing devices, sharper and better resolved eluted peaks were obtained with the chromatobox. However, the difference in resolution between the chromatobox and the column was not as significant as that observed with the 9 mL devices. This is not a very objective comparison as the media in the 9 and 50 mL devices were different, i.e. Capto S in the 9 mL devices and Capto Q in the 50 mL devices. However, purely based on intuition, it would be fair to expect the chromatobox to be more efficient when the ratio of bed height to column diameter is smaller. Incidentally, these ratios were 0.42 and 0.93 respectively for the 9 and 50 mL columns.

The results discussed above demonstrate that separation challenges with columns having small bed-heights relative to diameter could potentially be addressed by using a chromatobox according to one of the embodiments described herein, certainly at the scale examined. The flow-through and eluted peaks obtained with a chromatobox according to these Examples were sharper and less asymmetric than those obtained with its equivalent column, and peak resolution was superior. This could be attributed to superior flow-distribution and narrower solute residence time distribution. Overall, the chromatobox does look promising for large-scale separations using packed-beds with low bed-heights.

While the above description provides examples of one or more methods or systems, it will be appreciated that other methods or systems may be within the scope of the claims as interpreted by one of skill in the art.

NOTATION h Height of column plate/lateral channel (m)
us Superficial velocity (m s−1)
l Path length (m)
r Distance in radial direction (m)
r Residence time (seconds)
v Velocity (m s−1)
vr Radial velocity (m s−1)
vz Lateral velocity (m s−1)
z Length in lateral direction (m)

What is claimed is:

1. A chromatography device for removing a solute from a fluid, the device comprising:
    a first plate having an inlet and a first channel, the first channel extending from the inlet along a first channel length and a first channel width of a top surface of a chromatographic media, the first channel length extending at least a total lengthwise extent of the top surface;
    a chamber coupled to the first plate and housing the chromatographic media, the chamber having a leading edge for receiving the fluid from the first channel and a trailing edge, the chromatographic media being configured to remove the solute from the fluid as the fluid passes through the chromatographic media; and
    a second plate coupled to the chamber, the second plate having a second channel and an outlet, the second channel extending from the outlet along a length and a width of a bottom surface of the chromatographic media to collect the fluid exiting the bottom surface of the chromatographic media and direct the fluid to the outlet;
    wherein the first channel width extends a total widthwise extent of the top surface at the leading edge of the chamber to direct a fluid from the inlet over the top surface of the chromatographic media;
    wherein the first channel directs the fluid over the leading edge of the chamber in a direction that is transverse to a direction of flow of the fluid through the chromatographic media and the second channel directs fluid from the trailing edge of the chamber to the outlet in a direction that is transverse to the direction of flow of the fluid through the chromatographic media, and
    wherein the top surface of the chromatographic media has a top media surface area and the bottom surface of the chromatographic media has a bottom media surface area matching the top media surface area.

2. The chromatography device of claim 1, wherein the inlet is positioned on a first side of the device to receive fluid into the device and direct the fluid towards the first channel in a direction transverse to the direction of flow of the fluid through the first channel.

3. The chromatography device of claim 1, wherein the outlet is positioned on a second side of the device to receive the fluid from the second channel and direct the fluid out of the device in a direction transverse to the direction of flow of the fluid through the second channel.

4. The chromatography device of claim 1, wherein the inlet is laterally aligned with the leading edge of the chamber.

5. The chromatography device of claim 1, wherein the outlet is laterally aligned with the trailing edge of the chamber.

6. The chromatography device of claim 1, wherein the inlet is laterally offset from the leading edge of the chamber.

7. The chromatography device of claim 1, wherein the outlet is laterally offset from the trailing edge of the chamber.

8. The chromatography device of claim 1, wherein a width of the first channel increases along its length from the inlet to the leading edge of the chamber to distribute the fluid across the chromatographic media as the fluid exits the first channel.

9. The chromatography device of claim 8, wherein the width of the first channel increases along its length at a constant rate from the inlet to the leading edge of the chamber.

10. The chromatography device of claim 1, wherein a width of the second channel decreases along its length from the trailing edge of the chamber to the outlet to collect the fluid from the chamber.

11. The chromatography device of claim 10, wherein the width of the second channel decreases along its length at a constant rate from the trailing edge of the chamber to the outlet.

12. The chromatography device of claim 1, wherein the first channel comprises a structure to distribute the fluid across the first channel and over the leading edge of the chamber.

13. The chromatography device of claim 12, wherein the structure is a mesh.

14. The chromatography device of claim 12, wherein the structure is a plurality of pillars.

15. A chromatography device for removing a solute from a fluid, the device comprising:
    a first plate having a first channel extending from an inlet along a first channel length and a first channel width of a top surface of a resin, the first channel length extending a total lengthwise extent of the top surface;
    a chamber housing the resin, the fluid directed through the resin in a second direction to remove the solute from the fluid; and
    a second plate having a second channel extending from an outlet along a, length and a width of a bottom surface of the resin to collect a fluid flowing in a third direction after exiting the chamber;
    wherein the first channel width extends a total widthwise extent of the top surface at a leading edge of the chamber to direct a fluid from the inlet over the top surface of the resin,
    wherein the first direction and the third direction are transverse to the second direction, and
    wherein the top surface of the resin has a top resin surface area and the bottom surface of the resin has a bottom resin surface area matching the top resin surface area.

16. A method of removing a solute from a fluid, the method comprising:
    directing the fluid through a first plate in a first direction, the first plate having a first channel extending from an inlet along a first channel length and a first channel width of a top surface of a resin, the first channel length extending a total lengthwise extent of the top surface;

directing the fluid through the resin in a second direction to remove the solute from the fluid, the resin housed in a cavity of a chamber; and directing the fluid through a second plate in a third direction, the second plate for collecting the fluid from the resin;

wherein the first channel width extends a total widthwise extent of the top surface at a leading edge of the chamber to direct a fluid from the inlet over the too surface of the resin, wherein the first direction and the third direction are transverse to the second direction, and wherein the first surface of the resin has a first surface area and the second surface of the resin has a second surface area matching the first surface area.

\* \* \* \* \*